(12) United States Patent
Ohama et al.

(10) Patent No.: US 8,233,956 B2
(45) Date of Patent: Jul. 31, 2012

(54) MEDICAL DEVICE

(75) Inventors: Shinji Ohama, Ehime (JP); Eiichiro Izumi, Ehime (JP)

(73) Assignee: Panasonic Corporation, Osaka (JP)

( * ) Notice: Subject to any disclaimer, the term of this patent is extended or adjusted under 35 U.S.C. 154(b) by 341 days.

(21) Appl. No.: 12/395,041

(22) Filed: Feb. 27, 2009

(65) Prior Publication Data

US 2009/0227854 A1  Sep. 10, 2009

(30) Foreign Application Priority Data

Feb. 29, 2008  (JP) ................................. 2008-050767

(51) Int. Cl.
| A61B 5/05 | (2006.01) |
| A61B 5/00 | (2006.01) |
| H01R 13/62 | (2006.01) |
| G01F 1/64 | (2006.01) |
| G01N 33/00 | (2006.01) |
| G01N 27/26 | (2006.01) |
| G01N 1/00 | (2006.01) |
| B65D 81/00 | (2006.01) |

(52) U.S. Cl. ........ 600/345; 600/348; 600/365; 600/583; 600/584; 439/159; 422/68.1; 436/95; 204/402; 204/403.02; 205/792

(58) Field of Classification Search ........................ None
See application file for complete search history.

(56) References Cited

U.S. PATENT DOCUMENTS

| 5,514,097 A | 5/1996 | Knauer |
| 6,454,746 B1 | 9/2002 | Bydlon et al. |
| 2005/0106069 A1* | 5/2005 | Matsumoto et al. ............ 422/98 |
| 2008/0021291 A1* | 1/2008 | Zocchi .......................... 600/300 |
| 2010/0012530 A1* | 1/2010 | Watanabe et al. ............. 205/792 |
| 2010/0178703 A1* | 7/2010 | Creaven et al. ................. 436/43 |

FOREIGN PATENT DOCUMENTS

| JP | 11-76404 | 3/1999 |
| JP | 2000-237311 | 9/2000 |
| JP | 2002-502296 | 1/2002 |
| JP | 2003-114213 | 4/2003 |
| JP | 2004061209 A * | 2/2004 |
| JP | 2005-134190 | 5/2005 |
| JP | 3686083 | 6/2005 |
| WO | 98/55168 | 12/1998 |
| WO | 2006/000794 | 1/2006 |
| WO | 2008/016137 | 2/2008 |

* cited by examiner

*Primary Examiner* — In Suk Bullock
*Assistant Examiner* — Jennifer Wecker
(74) *Attorney, Agent, or Firm* — Wenderoth, Lind & Ponack, L.L.P.

(57) ABSTRACT

A medical device includes a connector which contacts a sensor to electrically connect the sensor with a measurement circuit in a medical device, a contact terminal which constitutes the connector, and a slide pin which ejects the sensor out of the medical device. The slide pin performs the operation of pushing up the contact terminal contacting the sensor as well as the operation of pushing the sensor out of the medical device. Since the contact terminal is completely lifted up by the inclined surface of the upper end part of the slide pin before the sensor is discarded, there occurs no reaction due to rebound of the contact terminal which might occur at the moment when the contact terminal of the connector is separated from the sensor, and thereby the sensor can be discarded so as to fall freely.

11 Claims, 8 Drawing Sheets

MEDICAL DEVICE

BACKGROUND OF THE INVENTION

The present invention relates to a medical device which performs measurement and inspection of, such as, blood and body fluid using a sensor for analyzing, such as, blood and body fluid, and more particularly, the invention relates to an improved mechanism for discarding the sensor.

DESCRIPTION OF THE RELATED ART

Many conventional medical devices which perform measurement and inspection using sensors for analyzing, such as, blood and body fluid have been used in such a manner that a user inserts a disposable sensor in a medical device, and pinches an edge of the sensor with his fingers to pull the sensor out of the medical device after measurement and inspection are completed, and then discards the sensor directly into a waste box or the like. As for a sensor discarding means used after measurement and inspection are completed, a discarding lever or a slide pin which is provided on a connector and a medical device is operated to push the sensor out of the medical device, and thereby the sensor is discarded.

FIGS. 8 and 9 are diagrams illustrating medical devices having conventional sensor discarding mechanisms.

FIG. 8 shows a conventional example corresponding to Japanese Published Patent Application No. 2003-114213, and FIG. 9 shows a conventional example corresponding to Japanese Published Patent Application No. 2005-134190.

The mechanical device having the conventional sensor discarding mechanism shown in FIG. 8 comprises a discarding lever 1, a connector 2, a slide pin 3, a sensor 4, a lower case 5, a base plate 6, and an upper case 7. A rib on the rear surface of the discarding lever 1 which is attached to the lower case 5 is engaged with the slide pin 3 of the connector 2. The user slides the discarding lever 1 with his finger along the arrow direction as the discarding direction, and thereby the slide pin 3 pushes the sensor 4 out of the medical device to discard the sensor 4.

On the other hand, the medical device having the conventional sensor discarding mechanism shown in FIG. 9 is used in such a manner that, similarly to FIG. 8, the user slides the discarding lever 1 with his finger along the arrow direction as the discarding direction, and thereby a discarding rib 1a on the rear surface of the discarding lever 1 which is attached to the lower case 5 pushes out the sensor 4 inserted in the connector 2 to discard the sensor 4. After the sensor 4 is discarded, the user releases his finger from the discarding lever 1, and thereby the discarding lever 1 and the discarding rib 1a are returned to their original positions with contraction of a compression spring 1b.

In the conventional medical device configured as described above, the sensor is discarded by simply pushing the sensor with the discarding lever or the slide pin which is attached to the connector and the medical device. However, depending on the speed of sliding the discarding lever, the sensor might jump out to an unexpected distance or in an unexpected direction due to a reaction caused by rebound of the contact terminal of the connector at the moment when the contact terminal is made apart from the sensor, leading to a fear that the blood or body fluid attached to the sensor might be scattered to the measurer or any other place. Under such discarding state, a biohazard, i.e., a safety problem, is concerned particularly when used in medical institutions and the like.

SUMMARY OF THE INVENTION

The present invention is made to solve the above-described problems, and has for its object to provide a medical device with which discarding of a sensor after completion of measurement and inspection can be safely and reliably performed by an individual or a medical institution which uses the medical device.

Other objects and advantages of the invention will become apparent from the detailed description that follows. The detailed description and specific embodiments described are provided only for illustration since various additions and modifications within the scope of the invention will be apparent to those of skill in the art from the detailed description.

In order to solve the above-described conventional problems, according to a first aspect of the present invention, there is provided a medical device which performs measurement and inspection using a sensor for analyzing components of blood or body fluid, comprising: a connector part which contacts the sensor to electrically connect the sensor with a measurement circuit in the medical device; a contact terminal which constitutes the connector part; and a discarding means which ejects the sensor out of the medical device; wherein the discarding means pushes the sensor out of the medical device to make the contact terminal contacting the sensor apart from the sensor.

According to a second aspect of the present invention, the medical device defined in the first aspect further includes a slide pin which constitutes the discarding means, a discarding lever which is provided outside the medical device, a joint plate which connects the slide pin and the discarding lever, and the slide pin moving in conjunction with the discarding lever to discard the sensor.

According to a third aspect of the present invention, in the medical device defined in the first aspect, the connector part includes a sensor detection part which sandwiches or presses the sensor to hold the same, and detects that the sensor is inserted, and the sensor detection part is formed of a metal or a resin.

According to a fourth aspect of the present invention, in the medical device defined in the second aspect, the slide pin has an inclined part which has an inclined surface at an upper end of the plane that pushes the sensor.

According to a fifth aspect of the present invention, in the medical device defined in the second aspect, the discarding lever has concavities and convexities formed at its surface.

According to a sixth aspect of the present invention, in the medical device defined in the second aspect, the discarding lever is configured such that an end portion thereof on the sensor ejection side is raised up.

According to a seventh aspect of the present invention, in the medical device defined in the second aspect, part or entirety of the discarding lever is formed of a transparent or semi-transparent material.

According to an eighth aspect of the present invention, in the medical device defined in the second aspect, the slide pin moves in the connector part.

According to a ninth aspect of the present invention, in the medical device defined in the first aspect, the discarding means and the connector part perform mutually relative operations to hold or discard the sensor.

According to a tenth aspect of the present invention, in the medical device defined in the ninth aspect, the discarding means holds the sensor when it is moved to an end in the connector part, and the discarding means discards the sensor when it is moved to the other end in the connector part.

According to an eleventh aspect of the present invention, there is provided a medical device having a measurement circuit which measures components of blood or body fluid using a sensor for analyzing the same, comprising: a connector part which contacts the sensor to electrically connect the sensor with the measurement circuit; a contact terminal which constitutes the connector part; and a discarding means which ejects the sensor out of the medical device; wherein a slide pin constituting the discarding means ejects the sensor which is held sandwiched or pressed by the connector part, to the outside of the medical device body after the slide pin makes the contact terminal apart from the sensor.

According to a twelfth aspect of the present invention, in the medical device defined in an eleventh aspect, the connector part has a sensor detection part which sandwiches or presses the sensor to hold the same and detects that the sensor is inserted, and the sensor detection part is formed of a metal or a resin.

According to a thirteenth aspect of the present invention, in the medical device defined in an eleventh aspect, the slide pin has an inclined part which has an inclined surface at an upper end of the plane that pushes the sensor.

According to a fourteenth aspect of the present invention, in the medical device defined in an eleventh aspect wherein the slide pin moves in the connector part.

According to a fifteenth aspect of the present invention, in the medical device defined in an eleventh aspect, the discarding means and the connector part perform mutually relative operations to hold or discard the sensor.

According to the present invention, a medical device which performs measurement and inspection using a sensor for analyzing components of blood or body fluid, comprises a connector part which contacts the sensor to electrically connect the sensor with a measurement circuit in the medical device, a contact terminal which constitutes the connector part, and a discarding means which ejects the sensor out of the medical device, wherein the discarding means pushes the sensor out of the medical device to make the contact terminal contacting the sensor apart from the sensor. Therefore, when discarding the sensor after completion of measurement and inspection, since the sensor is prevented from jumping out to an unexpected distance or in an unexpected direction, there is no fear of a biohazard due to the blood or body fluid attached to the sensor being scattered to the measurer, resulting in significant increases in stability and safety upon discarding of the sensor.

Further, according to the present invention, a medical device having a measurement circuit which measures components of blood or body fluid using a sensor for analyzing the same, comprises a connector part which contacts the sensor to electrically connect the sensor with the measurement circuit, a contact terminal which constitutes the connector part, and a discarding means which ejects the sensor out of the medical device, wherein a slide pin constituting the discarding means ejects the sensor that is held sandwiched or pressed by the connector part, to the outside of the medical device body after the contact terminal is made apart from the sensor. Therefore, when discarding the sensor after completion of measurement and inspection, since the sensor is prevented from jumping out to an unexpected distance or in an unexpected direction, there is no fear of biohazard due to the blood or body fluid attached to the sensor being scattered to the measurer, resulting in significant increases in stability and safety upon discarding of the sensor.

BRIEF DESCRIPTION OF THE DRAWINGS

FIG. 4 is a diagram illustrating a sensor discarding operation of the medical device of the first embodiment, wherein

FIG. 5 is a diagram illustrating an arrangement of contact terminals in a medical device according to a second embodiment of the present invention, wherein

FIG. 6 is a diagram illustrating an arrangement of contact terminals in a medical device according to a third embodiment of the present invention, wherein

DETAILED DESCRIPTION OF THE INVENTION

Hereinafter, preferred embodiments of medical devices of the present invention will be described in detail with reference to the drawings.

Embodiment 1

Figure 1:
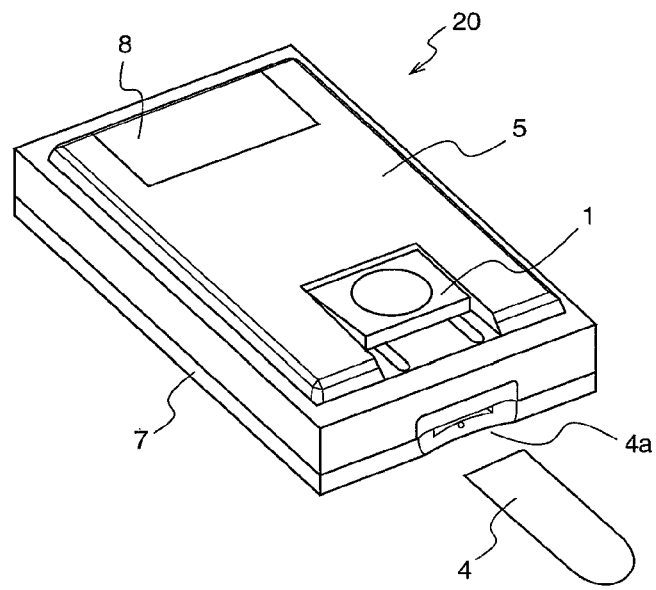
FIG. 1 is an overall perspective view of a medical device 20 according to a first embodiment of the present invention.

FIG. 1 is an overall perspective view of a medical device 20 according to a first embodiment of the present invention, which performs measurement and inspection of such as blood and body fluid using a sensor for analyzing such as blood and body fluid, wherein the medical device 20 is viewed from its bottom surface.

The medical device 20 has a device body which is obtained by combining major two parts, i.e., an upper case 7 and a lower case 5. A battery cover 8 covering a battery (not shown) which is placed in a battery storage concave part, and a discarding lever 1 constituting a discarding means for discarding a sensor 4 are attached to the lower case 5. The discarding lever 1 has a concave-convex configuration at its front surface, and a part or entirety thereof is formed of a transparent or semi-transparent material. Further, the discarding lever 1 is raised up at an end portion on the side of ejecting the sensor 4.

When performing measurement and inspection, the sensor 4 is inserted in a sensor insertion port 4a of the medical device 20, and the skin is pricked with a puncture device or the like, and then blood which exudes from the skin is applied to the sensor 4. The medical device 20 measures the components of the applied blood on the basis of a signal obtained from the sensor 4, and displays the measured value on a display unit (not shown). Thereafter, when discarding the sensor 4, the discarding lever 1 is operated to eject the sensor 4 from the sensor insertion port 4a to the outside of the medical device 20. A connector part is provided inside the sensor insertion port 4a.

Figure 2:
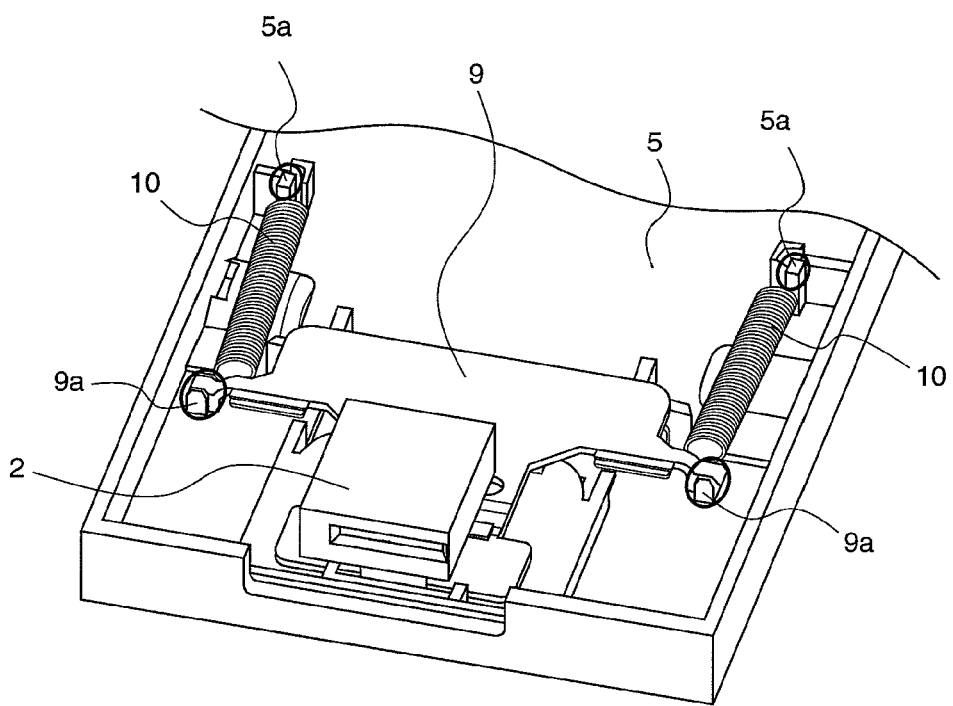
FIG. 2 is a major-part transparent perspective view illustrating a sensor discarding mechanism and its periphery in the medical device of the first embodiment.
Figure 8:
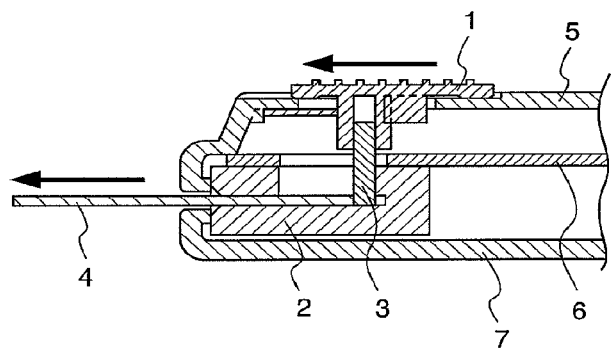
FIG. 8 is a cross-sectional view of a medical device having a conventional sensor discarding mechanism.
Figure 9:
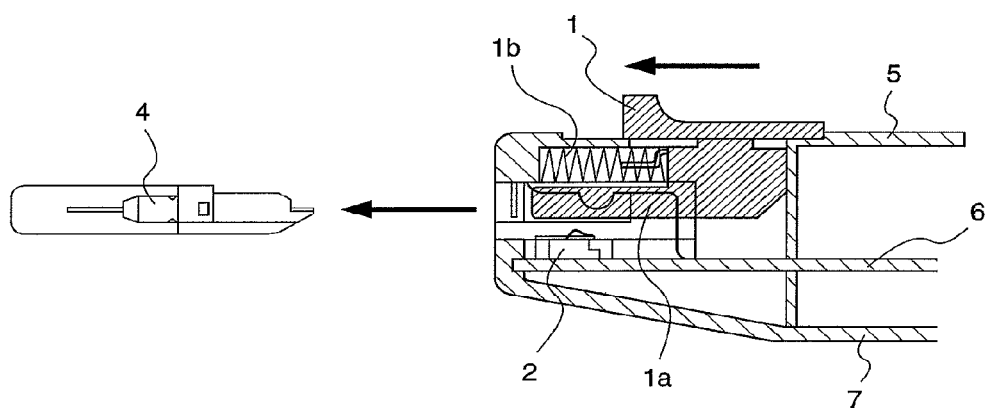
FIG. 9 is a cross-sectional view of another medical device having a conventional sensor discarding mechanism.

FIG. 2 is a major-part transparent perspective view illustrating a sensor discarding mechanism as the discarding means and its periphery in the medical device of the first embodiment, wherein the same constituents as those of the conventional example shown in FIG. 8 are given the same reference numerals, and the same functions are not repeatedly described.

A connector 2 constituting the connector part of the medical device 20 is solder-bonded in like manner as the substrate 6 which is embedded in the medical device having the conventional sensor discarding mechanism shown in FIG. 8, and a joint plate 9 is engaged with a slide pin 3 which constitutes the discarding means and is movable in the connector 2. Further, the joint plate 9 is engaged with the lower case 5 by right and left return springs 10. One ends of the right and left return springs 10 are hung on first sheet-plate hooks 9a of the joint plate 9 while the other ends thereof are hung on resin hooks 5a of the lower case 5, respectively. Although the discarding lever 1 is moved when discarding the sensor 4, it is returned to the initial position by that the right and left return springs 10 are contracted after the discarding.

Figure 3:
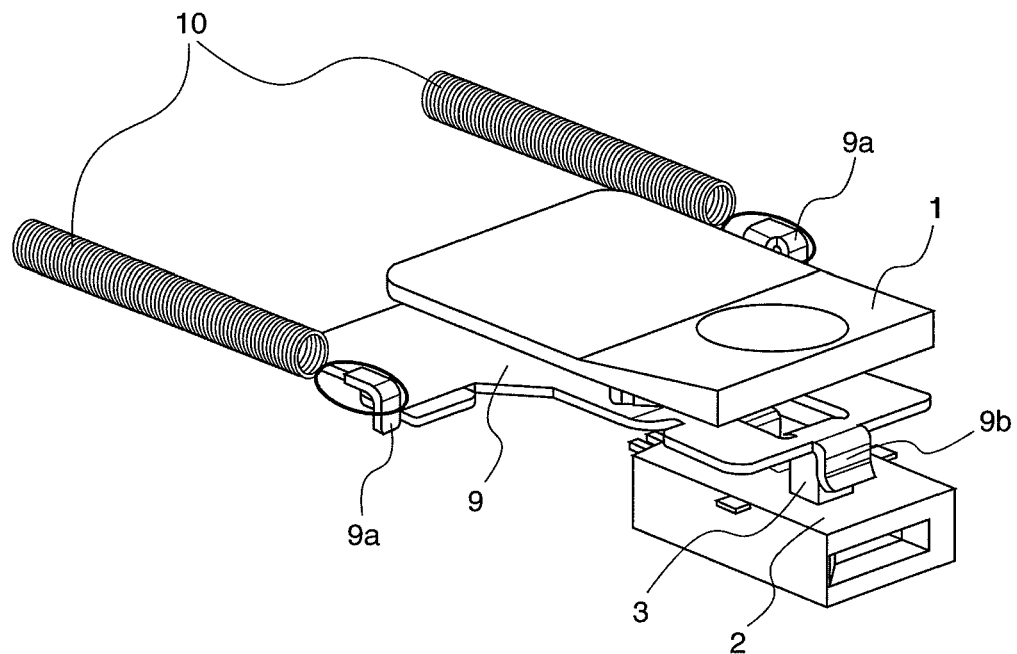
FIG. 3 is a major-part enlarged assembly view of the medical device of the first embodiment.

FIG. 3 is a major-part enlarged assembly view of the medical device of the first embodiment.

In FIG. 3, the slide pin 3 is engaged with the joint plate 9 by a second sheet-plate hook 9b of the joint plate 9, and the discarding lever 1 is screwed to the joint plate 9.

FIGS. 4(a), 4(b), 4(c), and 4(d) are cross-sectional views illustrating a sequence of sensor discarding operations by the connector 2 of the medical device of this first embodiment. The sensor 4 is held when the slide pin 3 is moved to one end in the connector 2 while it is discarded when the slide pin 3 is moved to the other end, according to the user's operating the discarding lever 1 with his finger.

Figure 4A:
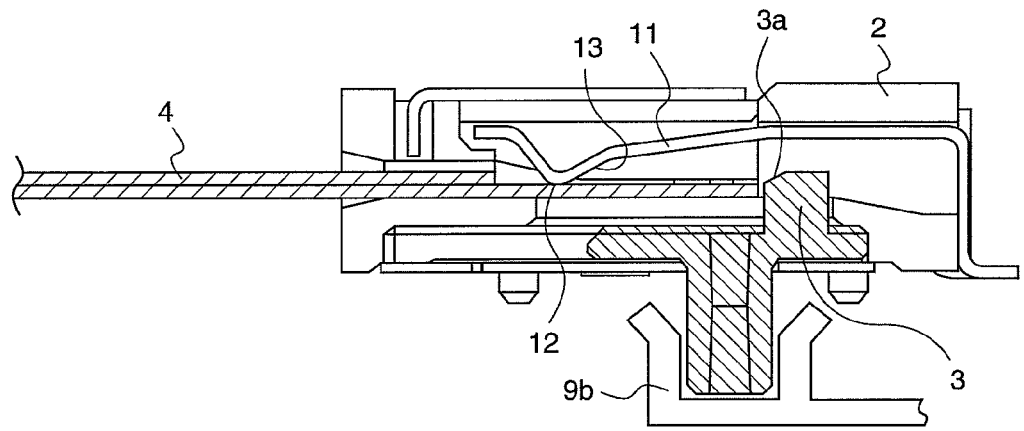
FIG. 4(a) is a cross-sectional view showing the state where the sensor is completely inserted in the medical device.

FIG. 4(a) shows the state where the sensor 4 is completely inserted in the sensor insertion port 4a of the medical device 20. The slide pin 3 is maintained at the initial position by the second sheet-plate hook 9b of the joint plate 9. At this time, the sensor 4 is pressed downward by the contact terminal 11 placed in the center of the connector 2 and other contact terminals (not shown). The contact terminal 11 contacts a terminal (not shown) of the sensor 4 at a contact point 12.

Figure 4B:
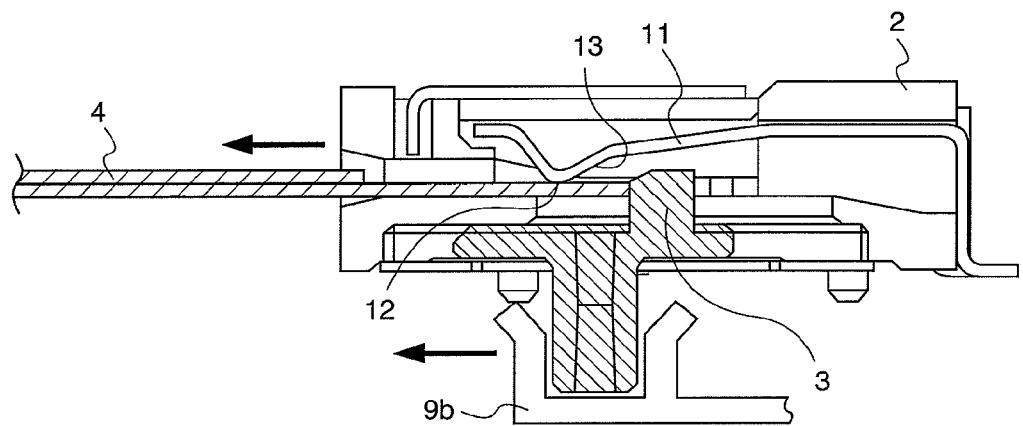
FIG. 4(b) is a cross-sectional view showing the state where a slide pin of the medical device pushes out the sensor.

Next, FIG. 4(b) shows the state where the slide pin 3 is in the middle of pushing out the sensor 4. The sensor 4 is being pushed out by the joint plate 9 moving the slide pin 3. At this time, the sensor 4 is being pushed out while subjected to a downward pressure by the contact terminal 11 and other contact terminals.

Figure 4C:
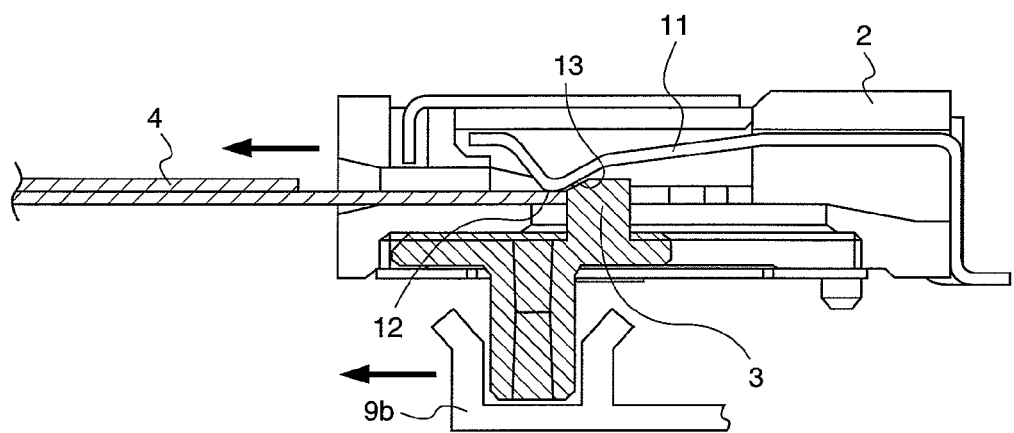
FIG. 4(c) is a cross-sectional view showing the state immediately before separation of the sensor from a terminal of the medical device.

Next, FIG. 4(c) shows the state immediately before separation of the contact terminal 11 from the sensor 4. The joint plate 9 moves the slide pin 3, and the contact terminal 11 almost runs on the inclined surface of the upper end portion of the plane which pushes the sensor 4 before discarding the sensor 4. The inclined part 13 of the contact terminal 11 contacts the inclined part 3a of the slide pin 3.

Figure 4D:
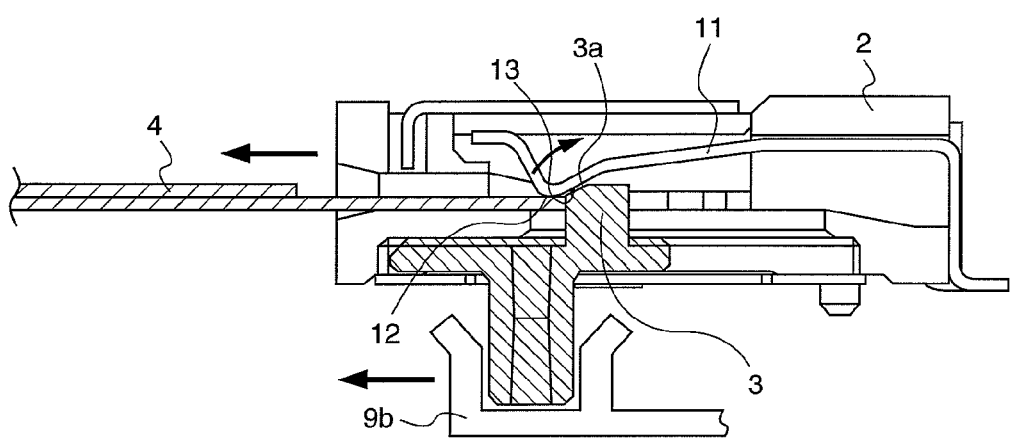
FIG. 4(d) is a cross-sectional view showing the state where the slide pin of the medical device pushes up the terminal to eject the sensor.

Finally, FIG. 4(d) shows the state where the inclined part 3a of the slide pin 3 lifts the contact terminal 11 upward to discard the sensor. The inclined part 13 of the contact terminal 11 contacts the inclined part 3a of the slide pin 3, and the contact terminal 11 is lifted upward by the inclined part 3a at the upper end of the slide pin 3 before discarding the sensor 4. Therefore, the sensor 4 and the contact terminal 11 are completely separated from each other, and there occurs no reaction due to rebound of the contact terminal which might occur at the moment when the contact terminal of the connector is separated from the sensor. Accordingly, the sensor 4 can be reliably discarded such that it is freely fallen.

While in this first embodiment the contact terminal 11 is lifted upward by the inclined part 3a of the slide pin 3, some or all of plural contact terminals may be lifted upward.

As described above, the medical device 20 of this first embodiment includes the connector 2 which contacts the sensor 4 to electrically connect the sensor 4 with the measurement circuit in the medical device 20, the contact terminal 11 which constitutes the connector 2, and the slide pin 3 which ejects the sensor 4 out of the medical device 20, and the slide pin 3 pushes the sensor 4 out of the medical device 20 to make the contact terminal 11 contacting the sensor 4 part from the sensor 4. Therefore, it is possible to prevent a reaction due to rebound of the contact terminal which might occur at the moment when the contact terminal of the connector is made to part from the sensor, and thereby the sensor can be reliably discarded such that it is freely fallen.

Embodiment 2

Figure 5A:
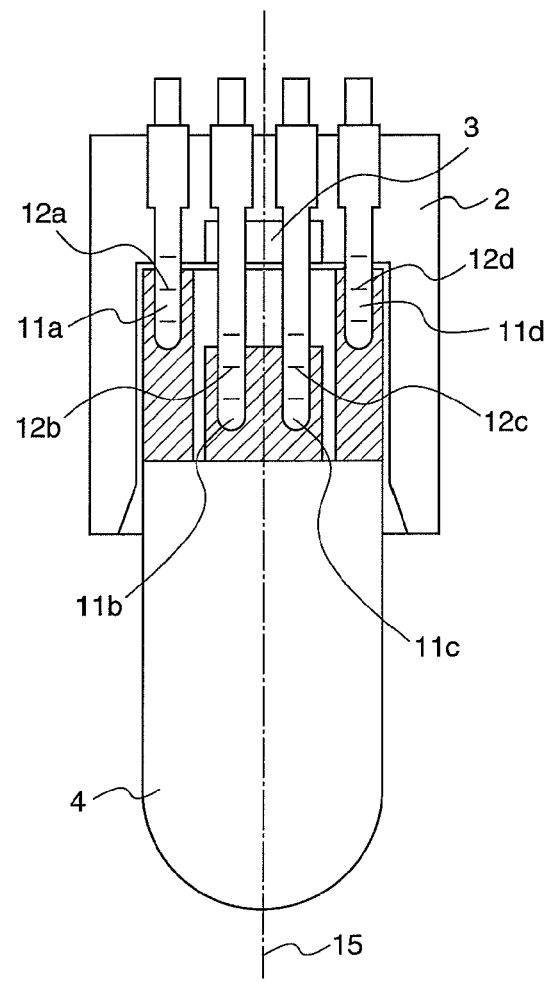
FIG. 5(a) is a plan view thereof.
Figure 5B:
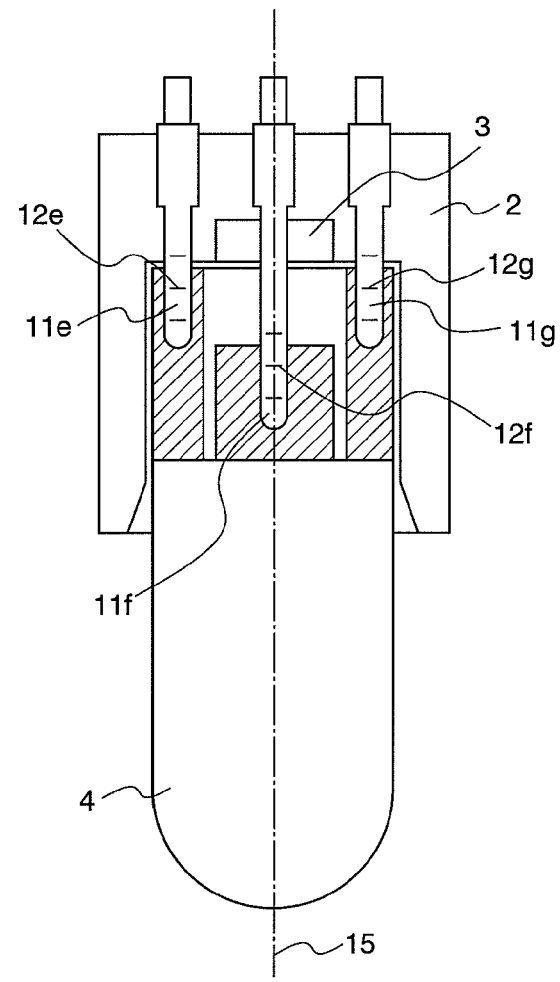
FIG. 5(b) is a plan view illustrating another arrangement of the contact terminals.

FIGS. 5(a) and 5(b) are plan views illustrating the arrangements of contact terminals in a medical device according to a second embodiment of the present invention.

FIG. 5(a) shows an arrangement of contact terminals 11a to 11d of a connector 2 in the medical device 20. While in FIGS. 5(a) and 5(b) the connector 2 has three to four contact terminals 11, the number of the contact terminals 11 may be one, or two or more. In FIGS. 5(a) and 5(b), the arrow shows the direction along which the sensor 4 is ejected.

Also in this second embodiment, as in the first embodiment, the respective contact terminals are lifted upward by the slide pin 3 during the ejection operation before the sensor 4 is discarded, and thereby the sensor 4 is completely separated from the contact terminals 11 (refer to FIGS. 4(c) and 4(d)).

Therefore, it is possible to prevent a reaction due to rebound of the contact terminals, which might occur at the moment when the contact terminals are made apart from the sensor. Accordingly, the sensor 4 can be reliably discarded such that it is freely fallen.

In addition, the arrangement of the contact terminals is also considered in this second embodiment as shown in FIGS. 5(a) and 5(b).

In FIG. 5(a), the contact terminals 11a and 11d (or the contact terminals 11b and 11c) are located symmetrically with respect to the center line 15 of the sensor 4 (corresponding to the center dashed line which longitudinally traverses the sensor 4 in FIG. 5(a)), and thereby the contact terminals prevent the sensor 4 from being ejected at random in the right and left directions when it is discarded to control the sensor so as to be discarded along the ejection direction (downward in FIG. 5(a)).

FIG. 5(b) shows an example other than FIG. 5(a), wherein the number of the contact terminals 11 is three. Also in the case of FIG. 5(b), the contact terminals 11e and 11g are located at symmetrical positions with respect to the center line 15 of the sensor 4, and thereby the sensor 4 is prevented from being ejected at random in the right and left directions, and controlled so as to be discarded along the ejection direction as in the case of FIG. 5(a).

Further, as shown in FIG. 5(a), the plural contact terminals 11a to 11d possessed by the connector 2 are arranged such that the distances between the respective contact terminals 11a to 11d in the direction perpendicular to the center line 15 of the sensor 4 are equal to each other. Further, as shown in FIG. 5(b), the contact terminals 11e to 11g are arranged such that the distances between the respective contact terminals 11e to 11g in the direction perpendicular to the center line 15 of the sensor 4 are equal to each other.

Furthermore, the distance between the contact points 12a and 12b of the contact terminals 11a and 11b is equal to the distance between the contact points 12c and 12d of the contact terminals 11c and 11d as shown in FIG. 5(a), and the distance between the contact points 12f and 12g of the contact terminals 11e and 11f is equal to the distance between the contact points 12f and 12g of the contact terminals 11f and 11g as shown in FIG. 5(b). Also when more contact terminals are provided, the distances between the contact points of the respective contact terminals which are located at symmetrical positions with respect to the center line of the sensor 4 are made approximately equal to each other.

Further, in FIG. 5(a), among the contact points 12a to 12d of the plural contact terminals 11a to 11d, the positions of the contact points 12b and 12c of the two contact terminals 11b and 11c in the center are protruded outward in the direction parallel to the plane surface of the sensor 4 relative to the positions of the contact points 12a and 12d of the other contact terminals 11a and 11d. However, among the contact points 12a to 12d of the plural contact terminals 11a to 11d, the positions of the contact points 12a and 12d of the contact terminals 11a and 11d other than the two contact terminals 11b and 11c in the center may be protruded outward in the direction parallel to the plane surface of the sensor 4 relative to the positions of the contact points 12b and 12c of the center contact terminals 11b and 11c.

Furthermore, in FIG. 5(b), among the contact points 12e to 12g of the plural contact terminals 11e to 11g, the position of the contact point 12f the one contact terminal 11f in the center is protruded outward in the direction parallel to the plane surface of the sensor 4 relative to the positions of the contact points 12e and 12g of the other contact terminals 11e and 11g. However, among the contact points 12e to 12g of the plural contact terminals 11e to 11g, the positions of the contact points 12e and 12g of the contact terminals 11e and 11g other than the one contact terminal 11f in the center may be protruded outward in the direction parallel to the plane surface of the sensor 4 relative to the position of the contact point 12f of the center contact terminal 11f.

Further, while in FIG. 5 three to four contact terminals are provided, more contact terminals may be provided. In this case, the plural contact terminals may be arranged such that the positions of the contact points of the even-numbered contact terminals from one end of the sequence of the contact terminals may be protruded outward in the direction parallel to the plane surface of the sensor relative to the positions of the contact points of the odd-numbered contact terminals, or such that the positions of the contact points of the odd-numbered contact terminals from one end of the sequence of the contact terminals may be protruded outward in the direction parallel to the plane surface of the sensor relative to the positions of the contact points of the even-numbered contact terminals.

As described above, according to the second embodiment, the contact terminals 11a to 11d are located at the symmetrical positions with respect to the center line 15 along the longitudinal direction of the sensor 4, and the distance between the contact points 12a and 12b of the contact terminals 11a and 11b is made equal to the distance between the contact points 12c and 12d of the contact terminals 11c and 11d. Therefore, the sensor 4 is prevented from being ejected at random in the right and left directions, and controlled so as to be discarded along the ejection direction.

Embodiment 3

Figure 6A:
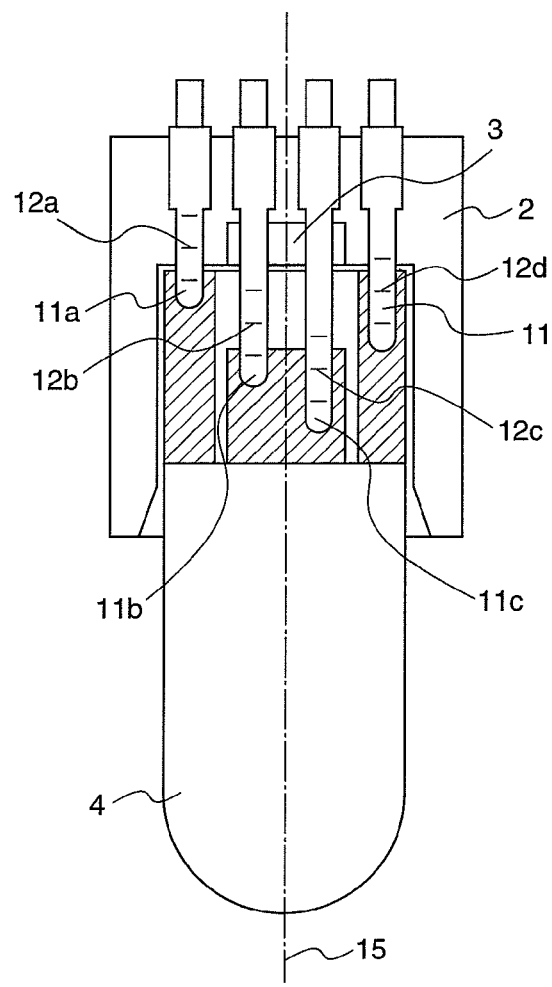
FIG. 6(a) is a plan view thereof.
Figure 6B:
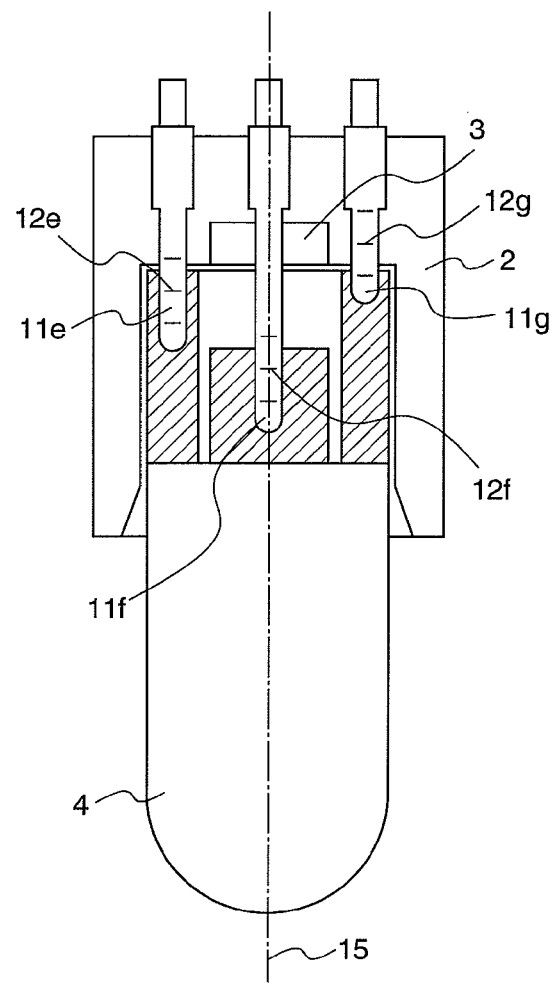
FIG. 6(b) is a plan view illustrating another arrangement of the contact terminals.

FIGS. 6(a) and 6(b) are plan views illustrating the arrangements of contact terminals in a medical device according to a third embodiment of the present invention.

FIG. 6(a) shows the arrangement of contact terminals 11a to 11d of the connector 2 in the medical device 20. While in FIGS. 6(a) and 6(b) the connector 2 has three to four contact terminals, the number of the contact terminals 11 may be one or two or more. In FIGS. 6(a) and 6(b), the arrow shows the ejection direction of the sensor 4.

Also in this third embodiment, as in the above-described first embodiment, the respective contact terminals are lifted upward by the slide pin 3 during the ejection operation before the sensor 4 is discarded, the sensor 4 and the contact terminals 11 are completely separated from each other (refer to FIGS. 4(c) and 4(d)).

Therefore, it is possible to avoid a reaction due to rebounds of the contact terminals, which might occur at the moment when the contact terminals are made apart from the sensor. Accordingly, the sensor 4 can be reliably discarded such that it is freely fallen.

In addition, the arrangement of the contact terminals is also considered in this third embodiment as shown in FIGS. 6(a) and 6(b).

In FIG. 6(a), the contact terminals 11a and 11b (or the contact terminals 11c and 11d) are positioned symmetrically with respect to the center line 15 of the sensor 4 (corresponding to the center dashed line which longitudinally traverses the sensor 4 in FIG. 6(a)). On the other hand, as shown in FIG. 6(a), since the distance between the contact points 12a and 12b of the contact terminals 11a and 11b and the distance between the contact points 12c and 12d of the contact terminals 11c and 11d are different from each other, the timings of making the respective contact terminals 11 apart from the sensor 4 are different from each other when discarding the sensor 4, and thereby the sensor 4 can be smoothly free-fallen and discarded.

FIG. 6(b) shows an example other than FIG. 6(a), wherein the number of the contact terminals 11 is three. Also in the case of FIG. 6(b), the contact terminals 11e and 11g are located at symmetrical positions with respect to the center line 15 of the sensor 4. On the other hand, since the distance between the contact points 12e and 12f of the contact terminals 11e and 11f is different from the distance between the contact points 12f and 12g of the contact terminals 11f and 11g, the timings of making the respective contact terminals 11 apart from the sensor 4 are different from each other when discarding the sensor 4 as in the case of FIG. 6(a), and thereby the sensor 4 can be smoothly free-fallen and discarded.

In FIGS. 6(a) and 6(b), in contrast to the cases of FIGS. 5(a) and 5(b) of the second embodiment, even when the contact points of the contact terminals are located asymmetrically with respect to the center line 15 of the sensor 4, the sensor 4 can be pushed out along the right and left side surfaces of the connector by lifting up all the contact terminals 11 from the sensor 4 in the early stage before discarding so that no contact pressure is applied to the sensor 4, and thereby the sensor 4 is prevented from jumping out to an unexpected direction or in an unexpected direction. For example, by making the angle of the inclined part 13 of each contact terminal 11 shown in FIG. 4(d) gentler with respect to the horizontal direction, the inclined part 13 of the contact terminal 11 is brought into contact with the inclined part 3a of the slide pin 3 in the earlier stage to lift the contact terminals 11 upward.

As described above, according to the third embodiment, the contact terminals 11a to 11d are located at the symmetrical positions with respect to the center line 15 along the longitudinal direction of the sensor, and the distance between the contact points 12e and 12f of the contact terminals 11e and 11f is made different from the distance between the contact points 12f and 12g of the contact terminals 11f and 11g. Therefore, when discarding the sensor 4, the timings of separating the respective contact terminals 11 from the contact points of the sensor are different from each other, and thereby the sensor 4 can smoothly frce fallen free-fall and be discarded.

Embodiment 4

Figure 7:
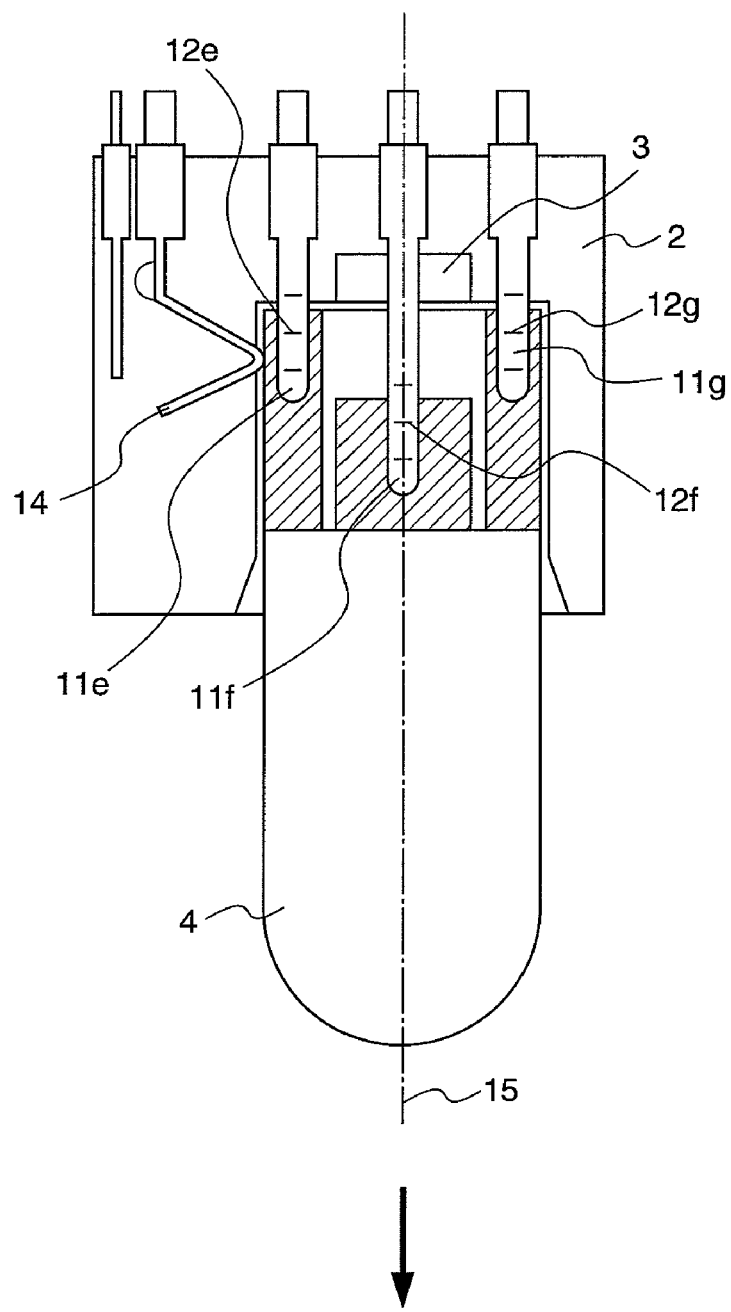
FIG. 7 is a plan view showing an arrangement of contact terminals in a medical device according to a fourth embodiment of the present invention.

FIG. 7 is a plan view illustrating the arrangement of contact terminals in a medical device according to a fourth embodiment of the present invention.

In FIG. 7, the contact terminals 11e and 11g are located at symmetrical positions with respect to the center line 15 of the sensor 4, and the contact terminals 11e to 11g are arranged such that the distances between the respective contact terminals 11e to 11g in the direction perpendicular to the center line 15 of the sensor 4 are equal to each other. In FIG. 7, the arrow shows the ejection direction of the sensor 4.

In this way, by locating the contact terminals 11e and 11g in symmetrical positions with respect to the center line 15 of the sensor 4 regardless of the number of the contact terminals 11, the sensor 4 is prevented from jumping out at random in the right and left directions, and controlled so as to be discarded along the ejection direction.

Further, the medical device of this fourth embodiment is provided with a sensor detection part 14 which pushes the sensor from the side to hold the same, in addition to the contact terminals 11e to 11g included in the connector 2 which electrically connects the sensor 4 and the measurement circuit. The sensor detection part 14 is a part of the connector 2 which sandwiches or presses the sensor 4 to hold the same, other than the contact terminals 11e to 11g, and it is formed of a metal or a resin.

The sensor 4 is released from the contact terminals 11e to 11g and the sensor detection part 14 as soon as the slide pin 3 pushes the sensor 4 out of the connector 2, thereby to prevent the sensor 4 from jumping out to an unexpected distance or in an unexpected direction.

While in this fourth embodiment the contact terminals are arranged similarly as shown in FIG. 5(b), the contact terminals may be arranged as shown in FIG. 5(a) or FIG. 6(a), 6(b). Further, the number of the contact terminals is not limited to three or four, but more terminals may be provided.

According to this fourth embodiment, the medical device is provided with the sensor detection part 14 which is a part of the connector 2, and sandwiches or presses the sensor 4 to hold the same, thereby to detect that the sensor is inserted. Therefore, it is possible to prevent the sensor 4 from jumping out to an unexpected distance or in an unexpected direction when discarding the sensor 4.

As described above, the medical device of the present invention prevents the sensor from jumping out to an unexpected distance or in an unexpected direction when the sensor is discarded after measurement and inspection, and thereby the fear of biohazard due to blood or body fluid attached to the sensor being scattered to the measurer is eliminated, resulting in significant increases in stability and safety.

What is claimed is:

1. A medical device which performs measurement and inspection using a sensor for analyzing components of blood or body fluid, said medical device comprising:
   a measurement circuit;
   a connector part configured to contact the sensor so as to electrically connect the sensor with said measurement circuit in said medical device;
   a plurality of contact terminals forming said connector part; and
   a discarding device configured to eject the sensor out of said medical device;
   wherein said discarding device includes a slide pin configured to push the sensor out of said medical device, and a discarding lever connected to said slide pin and being disposed on an outside surface of said medical device, said discarding lever configured to enable each contact terminal of said plurality of contact terminals to disengage from the sensor by moving each said contact terminal with said slide pin prior to the sensor being ejected by said discarding device.

2. A medical device as defined in claim 1 wherein said connector part includes a sensor detection part configured to sandwich or press the sensor to hold the sensor, and configured to detect that the sensor is inserted, and said sensor detection part is a metal or a resin.

3. A medical device as defined in claim 1 wherein said slide pin has an inclined part having an inclined surface at an upper end of a plane that is configured to push the sensor.

4. A medical device as defined in claim 1 wherein said discarding lever has concavities and convexities on a surface thereof.

5. A medical device as defined in claim 1 wherein said discarding lever has a first end portion and a second end portion, the first end portion being on a sensor ejection side, the second end portion being on a side opposite the sensor ejection side, and said first end portion is raised relative to said second end portion.

6. A medical device as defined in claim 1 wherein at least a part of said discarding lever is a transparent or semi-transparent material.

7. A medical device as defined in claim 1 wherein said slide pin is configured to move in said connector part.

8. A medical device as defined in claim 1 wherein said discarding device and said connector part are configured to perform mutually relative operations to hold or discard the sensor.

9. A medical device as defined in claim 8 wherein said discarding device holds the sensor when the sensor is moved to a first end in said connector part, and said discarding device discards the sensor when the sensor is moved to a second end in said connector part.

10. A medical device as defined in claim 1 wherein said plurality of contact terminals are disposed so as to be symmetrical about a center line along a longitudinal direction of the sensor.

11. A medical device as defined in claim 1 wherein said slide pin includes an inclined part that is configured to lift said plurality of contact terminals away from the sensor prior to discharging the sensor.

* * * * *